United States Patent [19]
Bourbon et al.

[11] Patent Number: 5,063,064
[45] Date of Patent: Nov. 5, 1991

[54] METHOD FOR INHIBITING OR DESTROYING SPERMATOZOA

[75] Inventors: Pierre Bourbon, Toulouse, France; Pierre Lagny, Kildare, Ireland; Pierre Billot, Neuilly/Seine, France

[73] Assignee: Atlantic Pharmaceutical Products Ltd., Celbridge, Ireland

[21] Appl. No.: 246,982

[22] Filed: Sep. 20, 1988

[51] Int. Cl.$^5$ ............................................. A61K 33/14
[52] U.S. Cl. .................................. 424/673; 424/676; 424/722; 514/841
[58] Field of Search ................ 426/673; 424/676, 722; 514/841

[56] References Cited

U.S. PATENT DOCUMENTS

| 4,097,590 | 6/1978 | Weisz | 424/151 |
| 4,321,277 | 3/1980 | Saurino | 514/643 |
| 4,473,547 | 9/1984 | Sipos | 424/52 |

FOREIGN PATENT DOCUMENTS 0055109 12/1981 European Pat. Off. .
0162574 4/1985 European Pat. Off. .

OTHER PUBLICATIONS

Chemical Abstracts, vol. 105, No. 25, dated Dec. 22, 1986, No. 218343x which concerns the effects of fluorides on oral microorganisms.

Primary Examiner—Leonard Schenkman
Attorney, Agent, or Firm—Fred A. Keire; Marilyn Brogan

[57] ABSTRACT

The invention is directed to a composition and a method for preparing the same which composition inhibits or destroys unicellular living organisms. The composition is effective as a spermicide and also in combating sexually transmitted diseases and as an antiseptic agent. The composition of the invention comprises lithium and ionic or ionizable fluorine, for example, lithium fluoride. A suitable excipient such as KATHON may also be present. The invention may, for example, comprise lithium fluoride and a spermicidal agent, such as a quaternary ammonium compound, for example, benzalkonium chloride.

9 Claims, No Drawings

METHOD FOR INHIBITING OR DESTROYING SPERMATOZOA

BACKGROUND OF THE INVENTION

The invention relates to the inhibition or destruction of unicellular living organisms such as protozoa, microbes, bacteria, gametes, fungi, yeasts or the like, and viruses. It hence relates especially to the technical fields of local contraception, of antibiotic therapy and of antisepsis, whether in the context of pharmacy or of cosmetics, as well as to that of disinfection.

Many substances and compositions that inhibit or destroy unicellular living organisms are already known. Unpublished European Patent Application No. 86/402,716.4, filed on 8.12.1986 and U.S. patent application Ser. No. 07/053 374 filed on 22.05.1987 by the applicant, mention such substances and compositions, and already teach that it is advantageous to use a compound that liberates $F^-$ ions alone or in combination with another primary active principle.

Moreover, lithium in the ionic state is already known in various therapeutic applications: in neurology, by way of a normothymic agent, in rhumatology or urology, by way of a uric acid-eliminating gent, in the field of dental care, by way of antiseptic PYOREX, registered trademark), and in the treatment of conditions of the airways in pneumology (THIOPHEOL).

Lithium fluoride is also already known as a chemical compound (The MERCK INDEX, TENTH EDITION, page 793, reference 5357). This compound is not, however, used by way of a medicinal product, or for inhibiting or destroying unicellular living organisms.

European Patent Application 0 055 109 describes an anti-caries composition comprising a fluorine salt and a carbohydrate. Among fluorides used by way of an anti-caries agent, lithium fluoride is mentioned. However, this document does not draw attention to any particular property due to the lithium fluoride for inhibiting or destroying microorganisms. In effect, in the combating of dental caries, fluorine has a known action, which does not consist in inhibiting or destroying microorganisms.

European Patent Application 0,162,574 describes a composition for oral/dental hygiene, such as a dentifrice, comprising a fluorine salt, a zinc salt, a buffering agent and an excipient. Among the fluorine salts referred to, lithium fluoride is mentioned. However, the fluorine salts are used in the context of that document only by way of anit-caries agent, as is taught in European Patent Application 0,055,109. Moreover, European Patent Application 0,162,574 also mentions the possibility of using a cationic surfactant agent by way of an antiseptic and antibacterial. However, this document does not describe a composition that makes it possible to inhibit or destroy microorganisms containing lithium fluoride.

The objects of the invention are to remedy the known drawbacks of the prior art, namely:

to reduce the necessary concentrations of active principles and/or activating principles while retaining the same efficacy, in order to limit or avoid side effects, to propose a composition that inhibits or destroys unicellular living organisms and which is safely administrable systemically or parenterally, to provide a new compound which is usable by way of a medicinal product or bactericidal, antibiotic, virucidal, antiseptic or disinfectant product or contraceptive, to propose other therapeutic applications of ionic lithium, and to provide a composition which is active against certain pathogenic organisms against which no remedy is known.

THE SUMMARY OF THE INVENTION

The invention hence proposes a spermicidal composition, a composition enabling sexually transmitted diseases to be combated, an antiseptic composition for the local disinfection of the human body—in particular of the skin, the mucosae, the limbs, etc—a composition for the disinfection of surfaces such as floors or instruments, and an antibiotic composition, and more generally a composition intended for destroying or inhibiting unicellular living organisms such as protozoa, microbes, bacteria, gametes, fungi, yeasts, viruses or the like, in therapeutic, contraceptive, sanitary or agricultural applications, characterized in that they contain:

ionic or ionisable lithium, or ionic or ionisable lithium and ionic or ionisable fluorine, in particular lithium fluoride, or A) lithium fluoride and B) a suitable excipient, or A) lithium fluoride, B) an active principle suitable for the application in question—in particular a surfactant detergent such as a quaternary ammonium compound, for example benzalkonium chloride, or a nonoxinol, or an antibiotic or a bactericide, or a sporicide, or a fungicide, or a virucide, or an antiseptic, or a disinfectant, or a spermicide—and C) a suitable excipient, or A) lithium fluoride, B) an active principle suitable for the application in question—in particular as referred to above, C) a preservative agent such as KATHON CG (registered trademark) and D) a suitable excipient.

A composition according to the invention can also contain in addition, another fluorine salt, in particular sodium fluoride.

KATHON comprises, as active ingredients, S-chloro-Z-methyl-4-isothiazoline-3-one in the amount of 1.125% and 2-methyl-4-isothiazoline-3-one in the amount of 0.375%, along with inert ingredients.

The invention also proposes a pharmaceutical composition containing ionic and ionisable fluorine and ionic or ionisable lithium, in particular lithium fluoride. The invention also proposes such a composition containing in addition, an active principle suitable for the therapeutic application in question—in particular a surfactant detergent such as quaternary ammonium compound, for example benzalkonium chloride or a nonoxinol, or an antibiotic, or a bactericide, or a spermicide, or a fungicide, or a virucide. The invention also proposes such a composition containing, in addition, an active principle with the exception of a zinc salt.

The invention also relates to the application of lithium $Li^+$ cations for manufacturing a product intended for destroying orinhibiting gametes—in particular spermatozoa—by way of a local contraceptive.

The invention also relates to the application of at least one compound capable of liberating $F^-$ ions and $Li^+$ ions—in particular lithium fluoride—for manufacturing a composition intended for combating sexually transmitted diseases.

The invention also relates to the application of at least one compound capable of liberating $F^-$ ions and $Li^+$ ions—in particular lithium fluoride—for manufacturing an antibiotic composition.

The invention also relates to the application of at least one compound capable of liberating F⁻ ions and Li⁺ ions—in particular lithium fluoride—for manufacturing an antiseptic or disinfectant composition.

The invention also relates to the application at least one compound capable of liberating F⁻ ions, at least one compound capable of liberating Li⁺ ions—in particular lithium fluoride—and at least one active principle—in particular a surfactant detergent such as a quaternary ammonium compound, for example benzalkonium chloride, or a nonoxinol—for manufacturing a spermicidal composition.

The invention also relates to the application of at least one compound capable of liberating F⁻ ions, at least one compound capable of liberating Li⁺ ions—in particular lithium fluoride—and at least one active principle—in particular a surfactant detergent such as a quaternary ammonium compound, for example benzalkonium chloride, or a nonoxinol—for manufacturing a compound intended for combating sexually transmitted diseases.

The invention also relates to the application of at least one compound capable of liberating F⁻ ions, at least one compound capable of liberating Li⁺ ions—in particular lithium fluoride—and at least one active principle—in particular a surfactant detergent such as a quaternary ammonium compound, for example benzalkonium chloride, or a nonoxinol—for manufacturing an antiseptic or disinfectant composition.

The invention also relates to the application of at least one compound capable of liberating F⁻ ions, at least one compound capable of liberating Li⁺ ions—in particular lithium fluoride—and at least one antibiotic principle for manufacturing an antibiotic product containing sufficiently low concentrations of F⁻, Li⁺ and antibiotic principle to enable it to be administered orally or parenterally.

The invention also relates to the application of at least one compound capable of liberating F⁻ ions, at least one compound capable of liberating Li⁺ ions—in particular lithium fluoride—at least one virucidal principle—in particular a surfactant detergent such as quaternary ammonium compound, for example benzalkonium chloride—for manufacturing a virucidal product containing sufficiently low concentrations of F⁻, Li⁺ and primary virucidal principle to enable it to be administered orally or parenterally.

The invention also relates to the application of at least one compound capable of liberating F⁻ ions, at least one compound capable of liberating Li⁺ ions—in particular lithium fluoride—and at least one bactericidal or antibiotic or fungicidal principle, for manufacturing a composition intended for combating pathogenic microorganisms such as chlamydiae, *Gardnerella vaginalis*, Ducrey's bacillus, *Candida albicans*, Aspergillus, Streptococcus, *Proteus vulgaris*, *Haemophilus influenzae*, *Pseudomonas aeruginosa*, *Escherichia coli*, Staphylococcus, Mycobacterium, *Neisseria gonorrhoeae*, Trichomonas, Treponema, *Sarcina lutea*, *Bacillus subtilis*, *Klebsiella pneumoniae* and Enterococcus.

The invention hence demonstrates, on the one hand, the surprising synergistic effect of the combination of F⁻ anions with Li⁺ cations for destroying or inhibiting unicellular living organisms, and by way of a medicinal product, contraceptive, cosmetic, bactericide, antibiotic, virucide or disinfectant, on the other hand, new applications given to Li⁺ ions, and finally a surprising activity of the combination of F⁻, Li⁺ and a primary active principle, enabling the concentrations to be reduced considerably and, in particular, products that are usable orally or parenterally to be obtained.

The invention also consists in having selected lithium fluoride among the possible fluorides mentioned in the prior art, and in having qualitatively and quantitatively demonstrated unexpected properties of lithium fluoride.

EXAMPLES AND PREFERRED EMBODIMENTS

The invention is illustrated by the examples below; the terminology and the methodologies used below have already been defined in unpublished European Patent Application No. 86/402,716.4, filed on 08.12.1986 and U.S. patent application Ser. No. 07/053 374 filed on 22.05.1987 by the applicant, and are integrated in the present specification and will hence not be fully specified again.

A benzalkonium chloride solution used in the trials contained a minimum of 90% by weight of C14 benzalkonium chloride of formula:

$(C_6H_5—CH_2—CH_3NCH_3—C_{14}H_{29}+. \ Cl^-)$ or myristyldimethylbenzylammonium chloride. It is also possible to use cocodimethylbenzylammonium chloride or alkyldimethylbenzylammonium chloride, or another quaternary ammonium chloride. All the percentages given are percentages by weight.

KATHON CG (registered trademark) is a known preservative marketed by ROHM AND HAAS COMPANY (U.S.A.), and consisting of a mixture of two isothiazolines identified according to IVPAC nomenclature as 5-chloro 2-methyl-4-isothiazolin-3-one and 2-methyl-4 isothiazolin-3-one.

I

APPLICATION OF THE INVENTION IN THE FIELD OF LOCAL CONTRACEPTION

EXAMPLE 1

European Patent Application No. 86/402,716.4 showed that F⁻ ions alone have a MIC (minimal inhibitory concentration), according to the SANDERS-CRAMER total spermicidal test according to IPPF standards of 5 ppm, equivalent to 0.0005%.

The same test carried out with lithium fluoride Lif alone showed that lithium fluoride alone has a MIC of the order of 3 ppm, equivalent to 0.0003%.

The same test carried out with lithium chloride LiCl alone showed that lithium chloride alone has a MIC of 20 ppm, equivalent to 0.002%.

A spermicidal effect of Li⁺ ions is hence observed. However, above all, the combination F⁻/Li⁺ achieves an unexpected synergistic effect.

The proportions of lithium fluoride contained in a spermicidal composition according to the invention must be such that the titre of lithium fluoride which it can liberate in vivo is greater than 2.5 mg/l, in order to be effective without reaching doses that cause side reactions.

The proportions liberated in vivo depend, of course, on the galenical form used. For example, the following galenical forms yield good results: cream, jelly, pessary, pad, soluble sheet, tablet, foam. For example:

| GALENICAL FORM | LiF (% by weight) |
| --- | --- |
| CREAM | 0.55 |

EXAMPLE 2

Furthermore, European Patent Application No. 86/402,716.4 showed that the addition of 1 milliliter of solution containing 0.0001% of F$^-$ anions (for example in the form of sodium fluoride) to 1 milliliter of composition containing benzalkonium chloride as primary active principle, in the context of the total spermicidal test according to IPPF standards, enables the MIC of the benzalkonium chloride to be lowered from a value of 0.006% (in the initial 1 milliliter) to 0.002% (in the initial 1 milliliter).

The same test carried out (in vitro) replacing the solution of 1 milliliter containing 0.0001% of F$^-$ anions by a solution of 1 milliliter containing 0.0001% of lithium fluoride enabled a MIC of benzalkonium chloride of 0.0009% (in the initial 1 milliliter) to be obtained.

A further boosting effect is hence observed. The maximal results (in vitro) were obtained with a solution of lithium fluoride at a concentration of 0.0001%.

The following galenical forms may be used: cream, jelly, pessary, pad, soluble sheet, tablet, foam. For example:

CREAM:
benzalkonium chloride: 0.90%
LiF: 0.55%

Excipients: emulsive agent, preservative such as KATHON (registered trademark), purified water, perfume qs. 100%.

JELLY: same formulations as the cream

Excipients: soluble derivatives of cellulose, glycerin, preservative such as KATHON (registered trademark), purified water, perfume qs. 100%.

PAD: impregnated with the cream defined above

TABLETS:
Benzalkonium chloride: 0.020 g
LiF: 0.010 g

Excipients: sodium bicarbonate, citric acid, colloidal silica, cellulose, magnesium stearate, lactose qs. 1 tablet.

SOLUBLE SHEET: same formulations as the cream

Excipients: polyvinilic alcohol, glycerin, preservative such as KATHON (registered trademark), purified water qs. 100%.

PESSARIES:
Benzalkonium chloride: 0.017 g
LiF: 0.010 g

Excipients: semi-synthetic glycerides, preservative such as KATHON (registered trademark) qs. 1 pessary.

A local contraceptive, in particular spermicidal, product according to the invention is characterized in that it contains between 0.20% and 0.75%—in particular, of the order of 0.55%—by weight of lithium fluoride and between 0.10% and 1.20% of benzalkonium chloride.

II

APPLICATION OF THE INVENTION FOR COMBATING THE MICROORGANISMS RESPONSIBLE FOR INFECTIONS SUCH AS SEXUALLY TRANSMITTED DISEASES.

EXAMPLE 3

Combating Chlamydiae

The methodology of the tests performed in order to demonstrate the application of the invention in the context of combating chlamydiae is that described by Professors F. CATALAN, P. SEDNAOUI, A. MILOVANOVIC et al., Institut A. FOURNIER, PARIS, already mentioned in unpublished European Patent Application No. 86/402,716.4

The test was performed on 12 strains of Chlamydia trachomatis originating from hospital sources, in particular from cases of urethritis. All the trials were performed in duplicate, and the results compared with those for a listed control strain.

It was first verified that lithium fluoride at a concentration of 1 mg/l does not have toxic activity with respect to MAC COY cells. In addition, since the threshold of cytotoxic activity of benzalkonium chloride is 0.01% with respect to MAC COY cells, benzalkonium chloride is not toxic either on MAC COY cells under the conditions of the trials carried out.

The MIC corresponds to the concentration of benzalkonium chloride at and above which the average number of colonies in Petri dishes containing the active substance is less than one tenth of the average number of colonies in Petri dishes without active substance.

The MIC of benzalkonium chloride alone varied with respect to the 12 wild-type strains tested, from 12 to 180 mg/l. The MIC of benzalkonium chloride with respect to the listed test strain is 18 mg/l.

The MIC of benzalkonium chloride to which 1 mg/ml of lithium fluoride has been added varied with respect to these same 12 strains tested, from 8 to 160 mg/l. The MIC of benzalkonium chloride to which 1 mg/ml has been added with respect to the listed test strain is 13 mg/l.

A big improvement of the results with lithium fluoride is hence observed.

EXAMPLE 4

Combating *Gardnerella vaginalis*

Two trials were carried out in order to illustrate the application of the invention in combating *Gardnerella vaginalis*.

In the first trial, the sample of bactericidal substance was incorporated directly in the specific culture edium of the microorganism. A concentration series of the bactericidal substance was prepared in the geometric ratio of 2, from 400 μg/ml to 1.56 μg/ml. The cell concentration used in the seeding of the Petri dishes was $10^{-3}$ per ml. A 24-hour incubation was performed at 37° C., and then, for each wild-type strain tested, the concentration of primary principle destroying all the microorganisms (see method of Professor F. CATALAN et al., Institut A. FOURNIER, PARIS) was determined. The trial was performed on 32 wild-type strains of *Gardnerella vaginalis* originating from hospital sources and with benzalkonium chloride and then nonoxinol 9 as active principles, and with sodium fluoride NaF at a concentration of 1 mg/l and then lithium fluoride LiF at a concentration of 1 mg/l as activating principles. The results obtained are correlated in the table below, which expresses the number of strains inhibited out of the 32 tested, in terms of the concentrations of primary active principle (benzalkonium chloride or nonoxinol).

| SUB-STANCE | Concentration in mg/l of primary active principle (benzalkonium chloride or nonoxinol) | | | | | | | | |
|---|---|---|---|---|---|---|---|---|---|
| | 1.56 | 3.125 | 6.25 | 12.5 | 25 | 50 | 100 | 200 | 400 |
| Benzalkonium chloride | 0 | 0 | 1 | 28 | 31 | 32 | — | — | — |
| Benzalkonium chloride + NaF (1 mg/l) | 0 | 0 | 7 | 30 | 32 | — | — | — | — |
| Benzalkonium chloride + LiF (1 mg/l) | 0 | 0 | 13 | 32 | — | — | — | — | — |
| Nonoxinol 9 | 0 | 0 | 0 | 0 | 4 | 6 | 10 | 25 | 32 |
| Nonoxinol 9 + NaF (1 mg/l) | 0 | 0 | 0 | 1 | 12 | 20 | 26 | 31 | 32 |
| Nonoxinol 9 + LiF (1 mg/l) | 0 | 0 | 0 | 1 | 16 | 25 | 30 | 32 | — |

This table illustrates the surprising boosting effect of lithium fluoride compared with sodium fluoride. In effect, at equal concentrations, the number of strains inhibited in the presence of LiF is always markedly greater than the number of strains inhibited in the presence of NaF. The totally lethal concentration for benzalkonium chloride falls from 50 mg/l when it is alone, to 25 mg/l in the presence of NaF, to 12.5 mg/l in the presence of LiF.

The second trial carried out was performed according to the contact methodology described in AFNOR standard T 72-151, by counting the strains surviving after a 15-min active substance/microbacterial solution contact followed by a filtration on a membrane (porosity 0.22 μm).

In this trial, 26 wild-type strains of *Gardnerella vaginalis* were tested, originating from hospital sources. The starting solution contained 0.1% of benzalkonium chloride, and was then diluted to $10^{-1}$, $10^{-2}$, $10^{-3}$ and $10^{-4}$. The results are summarized in the table below, which gives the total number of strains surviving (out of the 26 tested) in terms of the dilution.

| Dilution of the 0.1% strength solution | Benzalkonium chloride alone | Benzalkonium chloride + NaF (1 mg/l) | Benzalkonium chloride + LiF (1 mg/l) |
|---|---|---|---|
| $10^{-1}$ | 0 | 0 | 0 |
| $10^{-2}$ | 18 | 7 | 0 |
| $10^{-3}$ | 22 | 15 | 15 |
| $10^{-4}$ | 26 | 26 | 26 |

EXAMPLE 5

Combating *Trichomonas vaginalis*

The same methodology as in example 4 was used on 15 strains of Trichomonas vaginalis. The results are given in the following table, which indicates the number of strains inhibited out of the 15 tested, in terms of the concentrations of benzalkonium chloride:

| SUB-STANCE | Concentrations in mg/l of benzalkonium chloride | | | | | | | | |
|---|---|---|---|---|---|---|---|---|---|
| | 1.56 | 3.125 | 6.25 | 12.5 | 25 | 50 | 100 | 200 | 400 |
| Benzalkonium chloride | 1 | 3 | 9 | 13 | 15 | — | — | — | — |
| Benzalkonium chloride + LiF (1 mg/l) | 3 | 8 | 15 | — | — | — | — | — | — |

The MIC hence falls from 25 mg/l for benzalkonium chloride alone to 6.25 mg/l in the presence of LiF.

EXAMPLE 6

The MIC of benzalkonium chloride, alone and in the presence of LiF at a concentration of 1 mg/l, was determined with respect to other wild-type strains originating from hospital sources namely Streptococcus (6 strains), *Staphylococcus aureus* (8 strains), *Salmonella typhimurium* (3 strains) and *Sarcina lutea* (1 strain).

The MIC values obtained are summarized below:

| STRAIN | Benzalkonium chloride alone | Benzalkonium chloride in the presence of LiF at 1 mg/l |
|---|---|---|
| Streptococcus | 18–20 mg/l | 10 mg/l |
| Staphylococcus aureus | 1.56 mg/l | 0.90 mg/l |
| Salmonella typhimurium | 17 mg/l | 12 mg/l |
| Sarcina lutea | 15 mg/l | 11 mg/l |

EXAMPLE 7

Combating Ducrey's Bacillus

The methodology employed is that described by Professor F. CATALAN, P. SEDNAOUI, A. MILOVANOVIC et al., Institut A. FOURNIER, PARIS. The trials were performed on 8 wild-type strains of Ducrey's Haemophilus: The following results were recorded with respect to these strains:

| Primary active principle | MIC of the primary active principle with respect to DUCREY's bacillus (mg/l) | | |
|---|---|---|---|
| | Primary active principle alone | in the presence of NaF (1 mg/l) | in the presence of LiF (1 mg/l) |
| Benzalkonium chloride | 100 | 85 | 65 |
| Nonoxinol 9 | 150 | 132.5 | 127.5 |

Lithium fluoride hence proves to be a markedly better activating principle than sodium fluoride.

EXAMPLE 8

Combating *Candida albicans*

With the same methodology, trials were performed on hospital strains of *Candida albicans*:

| Primary active principle | Primary active principle | in the presence of LiF at 0.96 mg/l | in the presence of LiF at 0.96 mg/l and of KATHON CG (registered trademark) preservative at 0.234/mgl |
|---|---|---|---|
| Benzalkonium chloride | 50 mg/l | 135 mg/l | 2 mg/l |

EXAMPLE 9

Combating *Aspergillus niger*

With the same methodology, the following results were observed on hospital strains of *Aspergillus niger*:

| Primary active principle | Primary active principle alone | In the presence of LiF at 0.96 mg/l | In the presence of LiF at 0.96 mg/l and of KATHON CG (registered trademark) preservative at 0.234/mgl |
|---|---|---|---|
| benzalkonium chloride | 50 mg/l | 135 mg/l | 100/mg/l |

EXAMPLE 10

Combating pyogenic microorganisms

With the same methodology, the following results were observed on hospital strains of pyogenic microorganisms, namely β-haemolytic streptococcus, *Proteus vulgaris*, Haemophilus influenzae:

| Primary active principle | | MIC of the primary active principle | | |
|---|---|---|---|---|
| | | β-Haemolytic streptococcus | Proteus vulgaris | Haemophilus influenzae |
| Benzalkonium chloride | Alone | 50 mg/l | 25 mg/l | 200 mg/l |
| | In the presence of LiF at 1 mg/l and of KATHON CG$^R$ preservative at 0.4 mg/l | 25 mg/l | 18.5 mg/l | 150 mg/l |

The preferred galenical forms which can, for example, be used for combating STD's are the same as in the application by way of a spermicide.

Nonoxinol 9 may also be used as the active principle, for example:

PESSARY:
nonoxinol: 0.060 mg/l
LiF: 0.01 g
Excipients: semi-synthetic glycerides, preservative such as KATHON (registered trademark) qs. 1 pessary.

III

APPLICATION OF THE INVENTION IN THE FIELD OF ANTISEPSIS AND DISINFECTION

EXAMPLE 11

French standard NF T 72-150, March 1981 was followed by the trials carried out. The trials were performed on the strains defined by the AFNOR standard.

The results obtained on the strains defined by the AFNOR standard for benzalkonium chloride alone and for benzalkonium chloride with the addition of 1 mg/l of sodium fluoride were already given in unpublished European Patent Application 86/402,716.4, and have been recorded again.

These results are as follows:

| STRAIN | MINIMAL INHIBITORY CONCENTRATION (MIC) OF BENZALKONIUM CHLORIDE ALONE | MINIMAL INHIBITORY CONCENTRATION (MIC) OF BENZALKONIUM CHLORIDE IN THE PRESENCE OF NaF AT 1 mg/l |
|---|---|---|
| *Pseudomonas aeruginosa* CNCM A 22 | 31.25 mg/l | 18 mg/l |
| *Escharichia coli* CNCM 54 127 | 6.57 mg/l | 3 mg/l |
| *Staphylococcus aureus* Oxford strain CNCM 53 154 | 1.56 mg/l | 1.1 mg/l |
| *Streptococcus faecalis* CNCM 5 855 | 4 mg/l | 3.6 mg/l |
| *Mycobacterium smegmatis* CNCM7 326 | 30 mg/l | 26 mg/l |

The MIC obtained for benzalkonium chloride to which lithium fluoride was added at a concentration of 1 mg/l is as follows:

| STRAIN | MINIMAL INHIBITORY CONCENTRATION (MIC) OF BENZALKONIUM CHLORIDE IN THE PRESENCE OF LiF AT 1 mg/l |
|---|---|
| *Pseudomonas aeruginosa* | 15 mg/liter |

-continued

MINIMAL INHIBITORY CONCENTRATION (MIC) OF BENZALKONIUM CHLORIDE IN THE PRESENCE OF LiF AT 1 mg/l

| STRAIN | |
|---|---|
| CNCM A 22 Escherichia Coli | |
| CNCM 54 127 Staphylococcus faecalis Oxford strain | 2 mg/liter |
| CNCM 53 154 Streptococcus faecalis | 1.1 mg/liter |
| CNCM 5 855 Mycobacterium smegmatis CNCM 7 326 | 2.8 mg/liter |
| | 22 mg/liter |

EXAMPLE 12

The same trials as in example 11 were carried out on wild-type strains originating from hospital sources, namely 120 strains of Pseudomonas, 200 strains of *Escherichia coli*, 300 strains of Staphylococcus, 200 strains of Streptococcus and 50 strains of Mycobacterium.

The results obtained on the wild-type strains are summarized in the following table:

| STRAIN | MIC of benzalkonium chloride alone | MIC of benzalkonium chloride in the presence of LiF (1 mg/l) |
|---|---|---|
| Pseudomonas aeruginosa | 30 to 120 mg/l | 15 to 80 mg/l |
| Escherichia coli | 6 to 25 mg/l | 1.8 to 16 mg/l |
| Staphylococcus aureus | 2 to 13 mg/l | 0.8 to 8 mg/l |
| Streptococcus faecalis | 5 to 30 mg/l | 2.5 to 22 mg/l |
| Mycobacterium smegmatis | 32 to 120 mg/l | 20 to 90 mg/l |

EXAMPLE 13

The same trials as in example 12 were carried out on hospital strains of various microorganisms. The results obtained are as follows:

| STRAIN | MIC of benzalkonium alone in mg/l | MIC of benzalkonium chloride in mg/l in the presence of LiF at 1 ppm |
|---|---|---|
| Neisseria gonorrhoea | 1.15 | 0.60 |
| Trichomonas vaginalis | 1.30 | 0.90 |
| Candida albicans | 50 | 35 |
| Gardenerella vaginalis | 50 | 41 |
| Ducrey's bacillus | 75 | 62 |
| Streptococcus faecalis | 15 | 9 |
| Staphylococcus aureus | 1.56 | 1 |
| Aspergillus niger | 85 | 80 |
| Escherichia coli | 8 | 6.5 |
| Sarcina lutea | 11 | 7.5 |
| Bacillus subtilis | 8 | 5.4 |

EXAMPLE 14

Trials similar to those carried out in Examples 12 and 13 were carried out on 80 hospital strains of multi-resistant *Escherichia coli* producing plasmid β-lactamase. The results are as follows:

| | MIC of the primary active principle in mg/l | | |
|---|---|---|---|
| primary active principle | Primary active principle alone | in the presence of LiF at 0.96 mg/l | in the presence of LiF at 0.96 mg/l and of KATHON CG (registered trademark) preservative at 0.47 mg/l |
| Benzalkonium chloride | 8 to 12 | 6 to 9 | 4 to 6 |

EXAMPLE 15

The bactericidal activity of seven commercial local disinfectant antiseptics was compared with that of a foaming paste according to the invention, containing:
benzalkonium chloride: 2%
KATHON CG (registered trademark): 0.1%
lithium fluoride: 0.004%
sodium fluoride: 1.5%
excipient: foaming base:
and purified water: qs.

The methodology is that defined by AFNOR standard T 72-150, using the products under the conditions specified by the manufacturer as regards the concentrations and conditions of use.

In the table below, the sign + indicates that a growth of the microorganisms was observed, the sign ++ indicates that a very strong growth of the microorganisms was observed, and the sign − indicates that no growth of the microorganisms was observed.

Septivon-Lavril is a foaming solution marketed by Laboratoires CLIN MIDY (Paris, France).

Solubacter is a registered trademark denoting a foaming solution marketed by Laboratoires INNOTHERA (Arcueil, France).

Cyteal is a foaming solution marketed by Laboratoires SINBIO (Paris, France).

Hibiscrub is a foaming solution marketed by I.C.I.-PHARMA (Cergy, France).

Hibisprint is an alcoholic solution marketed by I.C.I.-PHARMA (Cergy, France).

Hexomedine is a registered trademark denoting a non foaming solution marketed by THERAPLIX S.A. (France).

Cetavlon is an antiseptic solution marketed by I.C.I.-PHARMA (Cergy, France).

The results obtained on *Escherichia coli, Staphylococcus aureus*, Streptococcus group A and Group C streptococcus are as follows:

| ANTISEPTIC TESTED | Escherichia coli | Staphylococcus aureus | Streptococcus group A | Streptococcus group C |
|---|---|---|---|---|
| Septivon-Lavril | − | ++ | − | − |
| Solubacter ® | − | − | + | − |
| Cyteal | − | + | + | − |
| Hibiscrub | − | − | − | − |
| Hibisprint | − | + | + | + |
| Hexomedine ® | − | − | − | − |
| Foaming paste according to the invention | − | − | − | − |
| Cetavlon | − | − | − | − |

EXAMPLE 16

Trials similar to those in example 15, but measuring the bacteriostatic activity (capacity to halt the proliferation of the microorganisms) of the antiseptics, were carried out. The foaming paste according to the invention was the same as in Example 15. The following results were obtained (with the same conventions as in Example 15):

| ANTISEPTIC PRODUCTS TESTED | 0.2 ml of innoculum contact time 10 mn | | | | 0.4 ml of innoculum contact time 20 mn | | | | 0.6 ml of innoculum contact time 30 mn | | | |
|---|---|---|---|---|---|---|---|---|---|---|---|---|
| | Distilled water | | Hard water | | Distilled water | | Hard water | | Distilled water | | Hard water | |
| | p+ | p− | p+ | p− | p+ | p− | p+ | p− | p+ | p− | p+ | p− |
| Crude cresol | S | S | S | S | R | S | S | R | R | R | R | R |
| Mercryl lauryle | R | S | R | R | R | R | R | R | R | R | R | R |
| Solubacter ® | S | S | R | S | R | R | R | R | R | R | R | R |
| Foaming paste according to the invention | S | S | S | S | S | S | S | S | S | S | S | S |
| Formaldehyde | S | S | S | S | S | S | S | S | S | S | S | S |
| Hexomedine ® | S | S | S | S | R | S | R | R | R | R | R | R |
| Hibisprint | S | S | S | S | S | S | R | R | R | R | R | R |
| Cetavlon | S | S | R | S | S | S | S | S | S | S | S | S |
| Zinc sulphate | R | R | R | R | R | R | R | R | R | R | R | R |

| ANTISEPTIC TESTED | Escherichia coli | Staphylococcus aureus | Streptococcus group A | Streptococcus group C |
|---|---|---|---|---|
| Septivon-Lavril | − | + | − | − |
| Solubacter ® | − | − | − | − |
| Cyteal | − | + | + | − |
| Hibiscrub | − | − | − | − |
| Hibisprint | − | + | + | − |
| Hexomedine ® | − | − | − | − |
| Foaming paste according to the invention | − | − | − | − |
| Cetavlon | − | − | − | − |

EXAMPLE 17

The resistance of *Pseudomonas aeruginosa* to various reputedly bactericidal active principles or commercial antiseptics was studied in terms of the hardness of the water and the presence or absence of proteins. The same trial was carried out on the foaming paste according to the invention (see Example 15). Mercryl Lauryle is a foaming solution marketed by Laboratoires LABAZ (Paris, France).

Cresol is the name given to three isomeric phenols, ortho, meta and para, $C_7H_8O$, immediate homologues of phenol, $HO—C_6H_4—CH_3$.

In the following table, R denotes resistant (a growth of colonies was observed), S denotes sensitive (no significant growth was observed), P+ means that proteins were added to the solvent and P− means that the solvent does not contain proteins.

The following galenical forms can be (for example, and without limitation) used by way of a dermatological local antiseptic (skin, mucosa, etc.):

FOAMING BAR:
benzalkonium chloride: 2%
LiF: 0.04%
NaF: 1.5%
Excipients: foaming synthetic base, preservative such as KATHON (registered trademark), purified water, perfume qs. 100%.

FOAMING PASTE: Same formulations as for the foaming bar, except for the excipient formulated as a paste.

MOISTURIZING CREAM:
benzalkonium chloride: 0.2%
LiF: 0.04%
NaF: 0.8%
Excipients: emulsive agent, moisturizing principle, wheatgerm oil, sweet almond oil, liquid paraffin, preservative such as KATHON (registered trademark), purified water qs. 100%.

IV

APPLICATION OF THE INVENTION IN THE FIELD OF ANTIBIOTIC THERAPY

EXAMPLE 18

The unicellular living organism chosen for the trials is *Pseudomonas aeruginosa* (wild-type strain originating from hospital sources).

The same methodology as for Examples 11 and 12 was followed. Bacteriostatic analyses were performed with a number of antibiotics belonging to benzylpenicillins, and aminopenicillins, and first and second generation cephalosporins, namely:

The bacterial inoculum and the dilution of antibiotic are placed in the plates, and incubated for 18 to 24 hours at 37° C.—the MIC is read in the depressions. Of 958 strains tested, 235 proved resistant to ticarcillin. Of these 235, 69 do not produce a β-lactamase and 166 produce a β-lactamase, namely: 50% a PSE β-lactamase, 17% a TEM β-lactamase, 28, an OXA 8-lactamase and 5% a cephalosporinase.

Three trials were performed per antibiotic and per bacterial inoculum. The trials were performed first with the antibiotics alone •trials a)§, and then with the addition of a dose of 1 mg/l of an aqueous solution of lithium fluoride •trials b)§ to the dilution of each one in every cup of every plate.

The results of the trials are gathered in the following table:

| TRIAL | ANTIBIOTIC | STRAIN Tic S βLac− MIC (μg/ml) | STRAIN Tic S βLac− MIC (μg/ml) | STRAIN Tic R βLac+ MIC (μg/ml) | | | |
|---|---|---|---|---|---|---|---|
| | | | | TEM | PSE | OXA | CEPHALO-SPORINASE |
| 1 | TICARCILLIN | 32 | 512 | 1024 | 4096 | 512 | 256 |
| 2a | AZLOCILLIN | 8 | 32 | 64 | 64 | 64 | 128 |
| 2b | +LiF 1 mg/l | 4 | 32 | 64 | 64 | 64 | 128 |
| 3a | PIPERACILLIN | 8 | 16 | 64 | 128 | 64 | 128 |
| 3b | +LiF | 8 | 8 | 64 | 64 | 64 | 128 |
| 4a | APALCILLIN | 4 | 16 | 16 | 64 | 32 | 16 |
| 4b | +LiF | 2 | 8 | 8 | 32 | 32 | 16 |
| 5a | CEFOPERAZONE | 8 | 16 | 32 | 64 | 64 | 64 |
| 5b | +LiF | 4 | 16 | 32 | 32 | 64 | 64 |
| 6a | CEFOTAXIME | 16 | 32 | 32 | 32 | 32 | 256 |
| 6b | +LiF | 8 | 16 | 32 | 16 | 16 | 256 |
| 7a | CEFTRIAXONE | 16 | 32 | 32 | 32 | 32 | 256 |
| 7b | +LiF | 8 | 16 | 32 | 16 | 32 | 128 |
| 8a | CEFSULODIN | 4 | 16 | 32 | 32 | 16 | 64 |
| 8b | +LiF | 4 | 16 | 32 | 16 | 16 | 34 |
| 9a | CAFTAZIDIME | 4 | 4 | 4 | 2 | 4 | 32 |
| 9b | +LiF | 2 | 4 | 4 | 2 | 4 | 32 |

Abbreviations used:
Tis S: sensitive to ticarcillin
Tic R: resistant to ticarcillin
βLac−: constitutive not producing β-lactamase
βLac+: constitutive producing β-lactamase
MIC: average MIC value a carboxypenicillin: ticarcillin,
three ureidopenicillins: azlocillin, piperacillin, apalcillin,
five cephalosporins: cefoperazone, cefotaxime, ceftriaxone, cefsulodin, ceftazidime.

The determination of the MIC was carried out by the microdilution method in liquid medium on plates. Aqueous solutions of each antibiotic are prepared in MUELLER HINTON broth, to obtain dilutions in a geometric ratio of 2. The solvent is sterile double-distilled water.

The preparation of the bacterial inoculum is made with a culture of *Pseudomonas aeruginosa*, with agitation on a water bath at 37° C. for 4 to 6 hours, giving $10^6$ bacteria/ml.

It is thus noted that the addition of lithium fluoride • comparison between trials a) and b) § enables the MIC with respect to the Tic S and Tic R strains of almost all the antibiotics to be decreased.

EXAMPLE 19

With the same methodology as above, the MIC values of benzalkonium chloride alone, in the presence of the KATHON CG (registered trademark) preservative (1 mg/l), and then in the presence of KATHON CG (registered trademark) (1 mg/l) and lithium fluoride (1 mg/l), were determined. 200 wild-type strains of *Pseudomonas aeruginosa* were tested.

The following results were observed:

| ANTIBIOTIC | STRAIN Tic S βLac− MIC (mg/l) | STRAIN Tic R βLac+ MIC (mg/l) | STRAIN Tic R βLac+ MIC (mg/l) | | | |
|---|---|---|---|---|---|---|
| | | | TEM | PSE | OXA | CEPHALOSPORINASE |
| TICARCILLIN | 32 | 512 | 1024 | 4096 | 512 | 256 |
| BENZALKONIUM CHLORIDE | 32 | 64 | 32 | 64 | 64 | 128 |
| +KATHON CG ® (1 mg/l) | 16 | 32 | 32 | 64 | 32 | 128 |
| +KATHON CG ® | 16 | 16 | 32 | 32 | 16 | 32 |

-continued

| ANTIBIOTIC | STRAIN Tic S βLac− MIC (mg/l) | STRAIN Tic R βLac+ MIC (mg/l) | STRAIN Tic R βLac+ MIC (mg/l) | | | |
|---|---|---|---|---|---|---|
| | | | TEM | PSE | OXA | CEPHALOSPORINASE |
| +(1 mg/l) | | | | | | |

A big improvement is hence observed in the presence of lithium fluoride, this being the case even on the strains producing cephalosporinase.

EXAMPLE 20

The same trial as in Example 19 was performed, but with nonoxinol 9 as the primary active principle; 200 wild-type strains of *Pseudomonas aeruginosa* were also tested. The results are as follows:

| ANTIBIOTIC | STRAIN Tic S βLac− MIC (mg/l) | STRAIN Tic R βLac+ MIC (mg/l) | STRAIN Tic R βLac+ MIC (mg/l) | | | |
|---|---|---|---|---|---|---|
| | | | TEM | PSE | OXA | CEPHALOSPORINASE |
| TICARCILLIN | 32 | 512 | 1024 | 4096 | 512 | 256 |
| NONOXINOL 9 | 64 | 128 | 128 | 64 | 128 | 256 |
| + KATHON CG ® (1 mg/l) | 32 | 128 | 128 | 64 | 128 | 256 |
| + KATHON CG ® + LiF (1 mg/l) | 32 | 64 | 64 | 64 | 64 | 128 |

EXAMPLE 21

The activity of CEFOTAXIME was tested, alone and then in the presence of lithium fluoride, with respect to pathogenic strains other than *Pseudomonas aeruginosa*.

The following table expresses the concentrations (mg/l) of cefotaxime inhibiting 50% of the strains.

| STRAIN | 50% INHIBITORY CONCENTRATION OF CEFOTAXIME ALONE | 50% INHIBITORY CONCENTRATION OF CEFOTAXIME IN THE PRESENCE OF LiF at 1 mg/l |
|---|---|---|
| *Escherichia coli* K12 J53 | 0.023 | 0.01 |
| *Escherichia coli* K12 PIP 111 | 0.023 | 0.023 |
| *Escherichia coli* K12 PIP 55 | 0.023 | 0.023 |
| *Escherichia coli* SOL | 0.18 | 0.18 |
| Klebsiella 1103 | 0.023 | 0.01 |
| Klebsiella U28 | 0.28 | 0.16 |
| Enterobacter T45 | 0.05 | 0.023 |
| Enterobacter P49 | 27.2 | 23.2 |
| *Proteus morganii* F20 | 0.01 | 0.01 |
| Serratia 1123 | 0.076 | 0.076 |
| Serratia M01117 | 0.30 | 0.30 |

EXAMPLE 22

The antibiotic activity of amoxicillin (type A penicillin), alone or combined with lithium fluoride, was tested with respect to hospital strains of *Haemophilus influenzae* producing β-lactamase.

The methodology employed is the same as above. The concentration of amoxicillin alone inhibiting the strains to 100% varied between 32 ppm and 64 ppm.

A concentration of 6 ppm of amoxicillin in the presence of 8 ppm of lithium fluoride enabled the strains to be inhibited to 100% in a time varying between 10 and 12 hours.

By way of comparison, a concentration of amoxicillin of 4 ppm in the presence of 1 ppm of clavulanic acid obtained, for example, by the proprietary pharmaceutical product known as AUGMENTIN and marketed by Laboratoires BEECHAM-SEVIGNE (Paris, France) enabled the strains to be inhibited to 100% in 24 hours.

It is hence found that the combination of LiF with amoxicillin enables the threshold of sensitivity of 16 ppm for *Haemophilus influenzae* to be crossed.

EXAMPLE 23

The antibiotic activity of amoxicillin, alone or combined with lithium fluoride, was tested with respect to hospital strains normally resistant to amoxicillin (inhibitory concentration greater than 16 ppm).

The results are as follows:

| STRAIN | 100% INHIBITORY CONCENTRATION OF AMOXICILLIN (ppm) | 100% INHIBITORY CONCENTRATION OF AMOXICILLIN IN THE PRESENCE OF LITHIUM FLUORIDE (LiF) | |
|---|---|---|---|
| | | Amoxicillin (ppm) | LiF (ppm) |
| Staphylococcus aureus | 32 | 8 | 8 |
| β-Haemolytic streptococcus | 16 | 4 | 8 |
| Klebsiella pneumoniae | 64 | 2 | 8 |
| Haemophilus influenzae | >128 | 32 | 8 |
| Escherichia coli (TEM plasmid) | >128 | 32 | 8 |

EXAMPLE 24

The antibiotic activity of ampicillin (type A penicillin of the beta-lactam family), alone or in the presence of lithium fluoride, was tested with respect to various strains.

The results are as follows:

EXAMPLE 25

COMBATING BRONCHOPULMONARY INFECTIONS

The same trials as in Examples 22 and 23 were carried out with tetracycline (cycline family), alone or in the presence of lithium fluoride, on wild-type hospital strains responsible for bronchopulmonary infections.

| STRAIN | MINIMAL INHIBITORY CONCENTRATION OF AMPICILLIN IN mg/l | MINIMAL INHIBITORY CONCENTRATIONS OF AMPICILLIN IN THE PRESENCE OF LITHIUM FLUORIDE (LiF) | |
|---|---|---|---|
| | | Ampicillin in mg/l | LiF in mg/l |
| Escherichia coli ATCC 25 922 | 4 | 2 | 1 |
| Streptococcus faecalis ATCC 25 212 | 8 | 4 | 5 |
| Escherichia coli (10 wild-type strains) | 2–8 | 1–4 | 5 |
| Streptococcus faecalis (10 wild-type strains) | 4–8 | 2 | 5 |
| Group C streptococcus | 32 | 8 | 1 |
| Pseudomonas aeruginosa | 16–32 | 4–8 | 5 |
| STRAINS RESISTANT TO AMPICILLIN | | | |
| Haemophilus influenzae (5 wild-type strains) | >128 | 32 | 5 |
| Staphylococcus aureus (10 strains) | >128 | 64 | 1 |
| Staphylococcus aureus (strains producing beta-lactamase) | >128 | 64 | 6 |
| Entrococcus faecium | >128 | 64 | 5 |
| Resistant Escherichia coli | 64 | 8 | 5 |
| MULTIRESISTANT STRAINS OFTEN PRODUCING BETA-LACTAMASE | | | |
| Pseudomonas aeruginosa | 16–32 | 4–8 | 0.8 |
| Escherichia coli | 64 | 8 | 0.8 |
| Staphylococcus aureus | >128 | 32 | 0.8 |
| Group C Streptococcus | 256 | 64 | 0.8 |
| Haemophilus influenzae | >128 | 32 | 0.8 |

| STRAIN | 100% INHIBITORY CONCENTRATION OF TETRACYCLINE (ppm) | 100% INHIBITORY CONCENTRATIONS OF TETRACYCLINE IN THE PRESENCE OF LITHIUM FLUORIDE (LiF) | |
|---|---|---|---|
| | | Tetracycline (ppm) | LiF (ppm) |
| Haemophilus influenzae | 4–8 | 2–4 | 4 |

| STRAIN | 100% INHIBITORY CONCENTRATION OF TETRACYCLINE (ppm) | 100% INHIBITORY CONCENTRATIONS OF TETRACYCLINE IN THE PRESENCE OF LITHIUM FLUORIDE (LiF) | |
|---|---|---|---|
| | | Tetracycline (ppm) | LiF (ppm) |
| *Klebsiella pneumoniae* | 0.5 | 0.25 | 2 |

EXAMPLE 26

COMBATING SKIN INFECTIONS

The same trials as in Examples 22, 23 and 25 were carried out on wild-type hospital strains responsible for skin infections with, on the one hand polymyxin B alone or in the presence of lithium fluoride, and on the other hand erythromycin (macrolide family), alone or in the presence of lithium fluoride.

The results are as follows:

| STRAIN | 100% INHIBITORY CONCENTRATION OF POLYMIXIN B (ppm) | 100% INHIBITORY CONCENTRATIONS OF POLYMIXIN B IN THE PRESENCE OF LITHIUM FLUORIDE (LiF) | |
|---|---|---|---|
| | | Polymixin B (ppm) | LiF (ppm) |
| Group C streptococcus | >128 | 64 | 8 |
| *Escherichia coli* | >128 | 64 | 2 |
| *Staphylococcus aureus* | >128 | 64 | 2 |

| STRAIN | 100% INHIBITORY CONCENTRATION OF ERYTHROMYCIN (ppm) | 100% INHIBITORY CONCENTRATIONS OF ERYTHROMYCIN IN THE PRESENCE OF LITHIUM FLUORIDE (LiF) | |
|---|---|---|---|
| | | Erythromycin (ppm) | LiF (ppm) |
| Group C streptococcus | 0.25 | 0.125 | 4 |
| *Escherichia coli* | 64 | 32 | 8 |

The various examples above show that the addition of lithium fluoride with certain antibiotics makes it possible to envisage the oral or parenteral administration of these antibiotics for combating pathogenic organisms which could not be effectively destroyed previously.

The invention hence relates to an antibiotic product that is administrable, in particular, orally, intravenously or, where appropriate, endolymphatically, characterized in that it contains, on the one hand of the order of 10 mg of lithium fluoride in 10 milliliters of injectable solution, and on the other hand an antibiotic, and an antibiotic product that is administrable intravenously, characterized by concentrations compatible with the physicochemical characters of the components and their possible toxicity.

We claim:

1. A method for inhibiting or destroying spermatozoa which comprises contacting the spermatozoa with a spermicidally effective amount of a composition which comprises ionic or ionizable lithium.

2. A method for inhibiting or destroying spermatozoa which comprises contacting the spermatozoa with a spermicidally effective amount of a composition which comprises ionic or ionizable fluorine and ionic or ionizable lithium.

3. A method for inhibiting or destroying spermatozoa which comprises contacting the spermatozoa with a spermicidally effective amount of a composition which comprises lithium fluoride and a suitable excipient.

4. A method for inhibiting or destroying spermatozoa which comprises contacting the spermatozoa with a spermicidally effective amount of a composition which comprises lithium fluoride, a spermicidal agent such as a quaternary ammonium compound, and a suitable excipient.

5. A method for inhibiting or destroying spermatozoa which comprises contacting the spermatozoa with a spermicidally effective amount of a composition which comprises lithium fluoride, a spermicidal agent selected from the group consisting of benzalkonium chloride or nonoxinol, a preservative agent, and a suitable excipient.

6. A method for inhibiting or destroying spermatozoa which comprises contacting the spermatozoa with the composition according to claim 5, and wherein the composition contains an additional fluorine salt.

7. A method for inhibiting or destroying spermatozoa which comprises contacting the spermatozoa with the composition according to claim 6, and wherein the additional fluorine salt is sodium fluoride.

8. A method for inhibiting or destroying spermatozoa which comprises contacting the spermatozoa with the composition according to claim 5 and wherein the composition contains between about 0.20% and 0.75% by weight of lithium fluoride and between about 0.10% and 1.20% by weight of benzalkonium chloride.

9. A method for inhibiting or destroying spermatozoa which comprises contacting the spermatozoa with the composition according to claim 8 and wherein the lithium fluoride is present in the amount of about 0.55% by weight.

* * * * *